United States Patent [19]
Kuehnle et al.

[11] Patent Number: 6,166,268
[45] Date of Patent: Dec. 26, 2000

[54] SELECTIVE OXIDATION AND THE SYNTHESIS OF HYDROXYL-CONTAINING AROMATIC COMPOUNDS

[75] Inventors: Adolf Kuehnle; Mark Duda, both of Marl, Germany

[73] Assignee: Creavis Gesellschaft fuer Technologie und Innovation mbH, Marl, Germany

[21] Appl. No.: 09/301,574

[22] Filed: Apr. 29, 1999

[30] Foreign Application Priority Data

| Apr. 30, 1998 | [DE] | Germany | 198 19 194 |
| Oct. 1, 1998 | [DE] | Germany | 198 45 136 |
| Dec. 18, 1998 | [DE] | Germany | 198 58 505 |

[51] Int. Cl.$^7$ ................................................. C07C 37/00
[52] U.S. Cl. .......................................................... 568/800
[58] Field of Search ............................................ 568/800

[56] References Cited

U.S. PATENT DOCUMENTS

| 5,001,280 | 3/1991 | Gubelmann | 568/716 |
| 5,055,623 | 10/1991 | Gubelmann et al. | |
| 5,110,995 | 5/1992 | Kharitonov et al. | |
| 5,672,777 | 9/1997 | Kharitonov et al. | |
| 5,756,861 | 5/1998 | Panov | 568/800 |
| 5,874,647 | 2/1999 | McGhee | 568/800 |
| 5,892,132 | 4/1999 | Rooks | 568/800 |

FOREIGN PATENT DOCUMENTS

| 195 06 843 | 8/1996 | Germany . |
| 195 08 843 | 9/1996 | Germany . |
| 195 45 042 | 8/1997 | Germany . |

OTHER PUBLICATIONS

"Selective Heterogeneous Epoxidations with Cp–Titanium Chloride Derived Microporous Silica Glasses", Tetrahedron vol. 51, No. 13 pp. 3787–3792, 1995.

"Hydroxylation of Benzene on ZSM5 Type Catalysts", 3rd World Congress on Oxidation Catalysis, R.K. Grasselli, S.T. Oy, A.M. Gaffney and J.E. Lyons (Editors) 1997 pp. 847–854.

"Method for the Calculation of Effective Pore Size Distribution in Molecular Sieve Carbon", Geza Horvath and Kunitaro Kawazoe, Journal of Chemical Engineering of Japan, vol. 16 No. 6, 1983 pp. 470–475.

"Tris (tert–butoxy)siloxy Complexes as Single–Source Precursors to Homogeneous Zirconia– and Hafnia–Silica Materials. An Alternative to the Sol–Gel Method", Karl W. Terry, Claus G. Lugmair, and T. Don Tilley, J.Am. Chem. Soc. 1997, 119, 9745–9756.

"Oxidative hydroxylation using dinitrogen monoxide: a possible route for organic synthesis over zeolites", Applied Catalysis, Elsevier Science Publishers B.V., Amsterdam, 1993, pp. 1–20.

"The Role of Surface α–Oxygen in Formation of Cation Radicals at Benzene Adsorption on ZSM–5", J.Phys. Chem. 1994, pp. 7548–7550.

G.I. Panov, et al., Catalysis Today 41, pp. 365–385, "Generation of Active Oxygen Species on Solid Surfaces. Opportunity for Novel Oxidation Technologies Over Zeolites," 1998.

*Primary Examiner*—Michael L. Shippen
*Attorney, Agent, or Firm*—Oblon, Spivak, McClelland, Maier & Neustadt, P.C.

[57] ABSTRACT

The invention relates to a process for preparing hydroxyl-containing aromatic compounds by catalytic oxidation.

12 Claims, No Drawings

SELECTIVE OXIDATION AND THE SYNTHESIS OF HYDROXYL-CONTAINING AROMATIC COMPOUNDS

BACKGROUND OF THE INVENTION

1. Field of the Invention

The present invention relates to the single-stage preparation of a hydroxyl-containing aromatic compound by selective catalytic oxidation of an aromatic hydrocarbon.

2. Discussion of the Related Art

To prepare a hydroxyl-containing aromatic compound, such as phenol, it has not been possible hitherto to transform a benzene directly into the corresponding hydroxyl compound by selective oxidation in a single stage and in high yield. Either the aromatic ring was not attacked at all by the oxidizing agent or it was destroyed by the action of the oxidizing agent. The principal products formed were carbon dioxide and coke.

From an economic point of view, it has only been possible hitherto to introduce a hydroxyl group into an aromatic system via a plurality of intermediate stages.

The cumene process has become established industrially for preparing phenols starting from benzenes. According to this process, usually, the cumene prepared from benzene and propene is peroxidized and the oxidation product is then cleaved into phenol and acetone.

In addition, a benzoic acid process starting from toluene is used, in which process the benzoic acid prepared from toluene can be decarboxylated to give phenol. The decarboxylation step, i.e. the loss of an organically bound carbon, however, consumes at this early stage any price advantage of toluene over benzene. The process is therefore only of interest if the intended product is benzoic acid and free capacities for preparing phenol are utilized.

Other processes for preparing phenol, e.g. via chlorobenzene (chlorination or oxychlorination of benzene) or the sulfonation process (preparation of benzenesulfonic acid) have proved to be uneconomic. Reasons for this were in part the unsatisfactory selectivity, corrosion problems and the production of unwanted by-products.

The cyclohexanol process (hydration of cyclohexene in the 1 st stage) is also uneconomical. The process goes through too many stages to arrive at the target product phenol.

For this reason, internationally, the majority of phenol is prepared via the above-mentioned cumene route. However, since in this process acetone is also produced, the cost-effectiveness of this process is dependent on the market prices for phenol and acetone.

In order to bypass the dependence on the coupled product acetone, many attempts concentrate on the selective oxidation of benzene or benzene derivatives. Thus, for example, U.S. Pat. Nos. 5,055,623, 5,672,777 and 5,110,995 describe the oxidation of benzene by dinitrogen monoxide on suitable catalysts.

The oxidizability of benzene by dinitrogen monoxide on vanadium 20 oxide/molybdenum oxide/tungsten oxide catalysts has already been known since 1982 (Iwamoto). Zeolite catalysts of the ZSM-5 type were discovered for the direct oxidation of benzene by dinitrogen monoxide in 1988 (Gubelmann, Rhone-Poulenc). The mode of action of zeolites is fundamentally due to their microporous channel system having pore diameters of the size of the molecules to be oxidized.

The use of iron-containing zeolite catalysts of the ZSM-5 type for oxidizing benzene by dinitrogen monoxide is described by Volodin, Bolshov and Panov in J. Phys. Chem. 1994, 98, 7548-7550.

The following documents also describe the oxidation on zeolites, in particular of the ZSM-5 type: 3rd *World Congress on Oxidation,* 1997 Elsevier Science, B. V., R. K Graselli et al., (Editors), M. Häfele et al. (University of Erlangen-Nuremberg) and G. I. Panov et al., Applied Catalysis A: General 98 (1993) 1–20.

The reaction which is most developed in terms of process engineering is that of dinitrogen monoxide on acid zeolites of the ZSM-5 and ZSM-11 type with various metal additions (e.g. iron). The reaction is usually carried out at atmospheric pressure and temperatures of 300–450° C.

It is a disadvantage of zeolites that because of their completely crystalline structure, the variation in pore size cannot be adapted continuously to the molecule to be oxidized, but is only possible stepwise, dependent on the crystal type which is established. This means that zeolites cannot be specifically adapted to the respective oxidation problem. The surface polarity, the setting of which makes certain reaction mechanisms conceivable, is also virtually invariable for zeolites. The literature, such as U.S. Pat. Nos. 5,110,995 or 5,055,623 describes one such zeolite type (the pentasils ZSM-5 and ZSM- I1) for preparing many phenol derivatives. Although zeolites or acidic zeolites can be modified by various metals, this can at best improve, but not completely solve the problem described above. Thus, for example, in an acid zeolite, a hydrogen atom can be exchanged for a sodium atom. In the iron-containing zeolite, in this case, no loss of activity was observed; whereas, when the iron is replaced by aluminum, the activity is decreased when a hydrogen atom is exchanged for a sodium atom. Overall, however, conversion rate and selectivity are still unsatisfactory.

Although changing other parameters, such as higher reaction temperature (zeolites are considered heat-stable up to about 800° C.) leads to higher benzene conversion rates, it also leads to lower selectivity and greater deactivation of the catalyst. Increasing the partial pressure of $N_2O$ can also increase the benzene conversion rate but this is likewise at the cost of selectivity. A gradual improvement can, at best, be achieved by increasing the partial pressure of benzene. The selectivity and the resulting amounts of phenol increase somewhat. Nevertheless, it is still desirable to increase the selectivity and degree of conversion further.

The relatively rapid coking of the catalyst, which occurs at the temperatures usually used leads to a loss of activity and the catalyst must, therefore, be regenerated relatively frequently (about every 48 hours).

The dinitrogen monoxide used for the catalytic oxidation of benzenes, in the processes described above, has to have a very high degree of purity. Contaminants such as oxygen or hydrophilic gases such as steam or ammonia can inactivate the zeolite catalyst to the point of inactivity. Only inert gases such as noble gases or nitrogen can be tolerated as admixtures.

Various sources of dinitrogen monoxide are suitable. The catalytic decomposition of ammonium nitrate at 100–160° C. using manganese, copper, lead, bismuth, cobalt and nickel catalysts gives a mixture of dinitrogen monoxide, nitrogen oxide and nitrogen dioxide, so that the gas cannot be used directly for oxidizing benzene.

Somewhat more expedient is oxidizing ammonia by oxygen on platinum oxide or bismuth oxide catalysts at 200–500° C. and reacting nitrogen oxide with carbon monoxide on platinum catalysts. However, in the first case, water is produced as by-product and in the second case carbon dioxide. Further, the dinitrogen monoxide prepared in this manner can not be used directly for the benzene oxidation. Similarly, the dinitrogen monoxide arising in the production of adipic acid cannot be used directly for the oxidation but must be subjected to a separate purification step. The oxygen present in the exhaust gas and the $NO_x$ interfere in particular.

The purity of the dinitrogen monoxide must also be seen against the background that zeolites absorb water, which decreases their catalytic activity. Although a few zeolite structures may be hydrophobized by dealumination, this further restricts the selection of suitable zeolites. The dealumination is, furthermore, an additional process step and leads to unwanted amorphous contents in the zeolite. In addition, the extent of the dealumination cannot be set specifically, so that with regard to the process, this must be determined empirically. This means that fluctuating quality grades of oxidizing agent, such as differing admixtures of steam, cannot be used.

SUMMARY OF THE INVENTION

It was, therefore, the object of the present invention to provide an economic process for the catalytic oxidation of aromatic compounds to give the corresponding hydroxyl compounds with high selectivities even at a low dinitrogen monoxide quality.

Surprisingly, it has been found that porous glasses can catalyze outstandingly the catalytic oxidation of aromatic compounds to give the corresponding hydroxyl compounds even when contaminated dinitrogen monoxide is used.

DESCRIPTION OF THE PREFERRED EMBODIMENTS

The present invention, therefore, relates to a process for preparing hydroxyl-containing aromatic compounds by catalytic oxidation; the catalytic oxidation of the aromatic compound is carried out by a dinitrogen-monoxide-containing gas in the presence of a porous glass at a temperature of 100–800° C.

The process, according to the invention, by using a corresponding porous glass, can be optimized to the respective conditions of use, such as the quality of the dinitrogen monoxide to be used or the type of aromatic compound.

This was not to be expected since the specialist literature for a high benzene conversion rate with simultaneously high selectivity to phenol suggests "special" zeolites, e.g. of the pentasil type such as for instance ZSM-5 and ZSM-11.

These zeolites have a three-dimensional structure ("cage structure") and, therefore, have a large surface area. However, the pore system of the porous glasses used in the process, according to the invention, has a predominantly different structure, so that, compared with zeolites, they generally do not permit a three-dimensional access and, therefore, one would expect a substantially decreased catalytic action (if any at all).

To what extent the channel system caused by the preparation process or the composition of the porous glasses used in the present process is the cause of their catalytic action may remain an open question but the process, according to the invention, even when low-quality dinitrogen monoxide is used, leads to high conversion rates with very high selectivities.

The dinitrogen-monoxide-containing gas used can be a mixture of from 5 to 100% by volume of dinitrogen monoxide and from 0 to 95% by volume of another gas.

The dinitrogen monoxide content of the gas used in the process, according to the invention, can likewise be from 80 to 100% by volume, together with from 0 to 20% by volume of another gas.

As other gases, use can be made of air, oxygen, nitrogen, noble gases, carbon dioxide, steam or ammonia or mixtures thereof.

The dinitrogen-monoxide-containing gas used can also contain organic or inorganic impurities, e.g. from an oxidation process (e.g. $N_2O$-preparation in situ or $N_2O$-containing exhaust gas from the preparation of adipic acid).

In a particular embodiment of the present invention the aromatic compound used is benzene but the oxidation of other aromatics, such as toluenes, xylenes or halogenated benzenes and also the oxidation of polynuclear aromatics, such as naphthalene, is also possible.

Surprisingly, on the surface of nonpolar-modified porous glasses, it has also been observed that the benzene conversion rate at below 375° C. (e.g. 350° C.) is virtually just as high as at above 375° C. The selectivity increases at lower temperatures as expected. With a zeolite-catalyzed system, the benzene conversion rate usually drops greatly with decreasing temperature. Under comparable conditions, therefore, a zeolite behaves considerably less expediently.

The process, according to the invention, is preferably carried out at temperatures of 200 to 700° C., particularly preferably of 250 to 550° C.

The porous glasses and microporous amorphous mixed metal oxides used in the process, according to the invention, can be prepared according to DE 195 06 843 A1.

The porous glasses used in the process, according to the invention, are prepared by the sol-gel process.

In one embodiment of the present invention, the porous glasses consist of 50–100% by weight of oxides of elements from main group 3, of main group 4, of subgroup 3 or of subgroup 4 of the Periodic Table of the Elements, including the lanthanides and actinides.

In another embodiment of the present invention, the mixed metal oxide matrix of the porous glasses can comprise at least 50% by weight of compounds of the element titanium, silicon, vanadium, aluminum, zirconium or cerium and/or up to 50% by weight of one or more metal oxides in very fine to atomic distribution selected from the group of the metals molybdenum, tin, zinc, vanadium, manganese, iron, cobalt, nickel, arsenic, lead, antimony, bismuth, ruthenium, rhenium, chromium, tungsten, niobium, hafnium, lanthanum, cerium, gadolinium, gallium, indium, thallium, silver, copper, lithium, potassium, sodium, beryllium, magnesium, calcium, strontium and barium.

Preferably, the mixed metal oxide matrix of the porous glasses comprises at least one, particularly preferably at least two, of the compounds selected from the group $SiO_2$, $TiO_2$, $Al_2O_3$, vanadium oxide, zirconium oxide, cerium oxide, spinel, mullite, silicon carbide, silicon nitride and titanium nitrite.

Furthermore, the mixed metal oxide matrix can additionally comprise up to 10% by weight of one of the metals platinum, rhodium, iridium, osmium, silver, gold, copper, nickel, palladium and cobalt in highly disperse form in metallic or oxidized state.

The porous glasses are obtainable by acid- or fluoride-catalyzed linear polymerization or polycondensation of hydrolyzable soluble compounds of the above-mentioned metals and oxides. Preferably, use is made of alkoxy, mixed alkoxyalkyl, alkoxyoxo or acetylacetonate derivatives of the described metals or metal oxides in the acid to neutral pH range in the sol-gel process. This is followed by mild drying and slow calcination; the end of the calcination being at a temperature of from 120 to 800° C.

An alternative method of preparation for this type of compound is the thermolysis process discussed by K. W. Terry et al., *J. Am. Chem. Soc.* 119, 9745–9756 (1997). However, 5 a disadvantage here, in comparison with the sol-gel process, is the decreased possibility of variation during preparation, so that in the final product only a very few element ratios are possible.

The production of nonpolar or hydrophobic porous glasses follows, for example, from the patent DE 195 45 042 A1. The polarity of the inner and outer surfaces of porous glasses can be set, for example, by copolycondensing alkylsilanes or aryloxysilanes having non-hydrolyzable alkyl or aryl groups R' of the type R'—Si(OR)$_3$ with the other components of the sol-gel process.

R and R' can be identical or different and are preferably aliphatic hydrocarbon radicals having up to 6 carbon atoms, such as methyl, ethyl or isopropyl groups or phenyl radicals.

The metal oxide reacted with this non-hydrolyzable group originates from the above-mentioned listing of metals. As ligands for the starting compound, that is the soluble metal compound, use is preferably made of halides, alkoxides, oxyalkoxides, carboxylates, oxalates, nitrates, sulfates, sulfonates, acetylacetonates, glycolates or aminoalkoxylates. The base material is $SiO_2$, $Al_2O_3$, $TiO_2$ or $ZrO_2$.

The use of hydrophobized porous glasses is advantageous, in particular, in the event of a high water content of the dinitrogen monoxide, since this ensures a constant high selectivity.

In addition to porous glasses, fluxes can also be used. These are also taken to mean support systems or mixtures based on $SiO_2$ or $Al_2O_3$. The use of a combination of porous glasses and (crystalline) zeolites is likewise possible without loss of conversion rate and selectivity, as shown in the examples.

The pore size and the total surface area of the glasses used are of importance. The mean pore size should be between 0.1 and 1 nm, determined as reported by Horvath and Kawazoe *J. Chem. Eng.* Jpn. 16 470 ff.(1983).

The total surface area of the porous glasses in the dry state is preferably at least about 50 m$^2$/g, particularly preferably from about 50 to 5000 m$^2$/g, most preferably from about 75 to about 1500 m$^2$/g, in each case determined by the BET-method according to W. F. Maier et al., *Tetrahedron* 51 3787 ff (1995). In accordance with the above method, the determination of BET surface was carried out at 77 K under nitrogen, using the continuous flow method, and a Coulter Omnisorp 360 sorptometer. The samples were previously heated at about 523° K and 5·10$^{-4}$Pa for 12–15 hours. The term "about" is used to denote, throughout the present application, a 10% deviation from the stated value.

Having generally described this invention, a further understanding can be obtained by reference to certain specific examples which are provided herein for purposes of illustration only and are not intended to be limiting unless otherwise specified.

The following Examples are also recited in the priority documents, German Patent Applications 198 19 194.4, filed Apr. 30, 1998; 198 45 136.9, filed Oct. 1, 1998; and 198 58 505.5, filed Dec. 18, 1998, which are incorporated herein by reference in their entirety.

EXAMPLES

1. Preparation of porous glasses 1.1 Zirconium dioxide-silicon dioxide glass 1 ml of tetrabutoxyzirconium, 10 ml of tetraethoxysilane and 8 ml of ethanol were dissolved successively in one another and 2 ml of 8 N hydrochloric acid were added with stirring. After gel formation had taken place, the material was heated to 65° C. at a heating rate of 0.5° C./min, kept for 3 hours at 65° C., heated at a heating rate of 0.2° C./min to 250° C. and calcined at this temperature for a further 3 hours. The product exhibited a monomodal pore distribution.

BET: 500 m$^2$/g

Pore diameter: 0.74 nm 1.2 Aluminum oxide-zirconium dioxide-silicon dioxide glass 0.45 ml of triisobutylaluminum, 2.01 ml of tetra-n-propoxyzirconium, 27.5 ml of tetraethoxysilane and 25 ml of ethanol were dissolved successively in one another and 4.5 ml of 0.4 N hydrochloric acid were added in the course of 10 minutes with stirring. In the course of this, the temperature increased to 55° C. After gel formation had taken place and after slow preliminary drying at room temperature, the material was heated to 65° C. at a heating rate of 0.5° C./min, kept at 65° C. for 3 hours, heated at a heating rate of 0.2° C./min to 300° C. and calcined at this temperature for a further 3 hours. The product exhibited a monomodal pore distribution.

BET: 290 m$^2$/g

Pore diameter: 0.69 nm 1.3 Zirconium dioxide-silicon dioxide glass 1 ml of tetrabutoxyzirconium, 10 ml of tetraethoxysilane and 8.4 ml of ethanol were dissolved successively in one another and 2 ml of 2 N hydrochloric acid were added with stirring. After gel formation had taken place, the material was heated to 65° C. at a heating rate of 0.5° C./min, kept at 65° C. for 3 hours, heated at a heating rate of 0.2° C./min to 250° C. and calcined at this temperature for a further 3 hours. The product exhibited a monomodal pore distribution.

BET: 250 m$^2$/g

Pore diameter: 0.65 nm 1.4 Vanadium oxide-silicon dioxide glass 1.2 g of vanadyl acetylacetonate, 10 ml of tetraethoxysilane and 8 ml of 1–3 ethanol were dissolved successivefully in one another and 2 ml of 8 N hydrochloric acid were added with stirring. After gel formation had taken place, the material was heated to 65° C. at a heating rate of 0.5° C./min, kept at 65° C. for 3 hours, heated at a heating rate of 0.2° C./min to 250° C. and calcined at this temperature for a further 3 hours. The product exhibited a monomodal pore distribution.

BET: 550 m$^2$/g

Pore diameter: 0.66 nm 1.5 Iron-containing silicon dioxide glass 1.2 g of iron acetylacetonate, 10 ml of tetraethoxysilane and 8 ml of ethanol were dissolved successively in one another and 2 ml of 8 N hydrochloric acid were added with stirring. After gel formation has taken place, the material was heated to 65° C. at a heating rate of 0.5° C./min, kept at 65° C. for 3 hours, heated at a heating rate of 0.2° C./min to 230° C. and calcined at this temperature for a further 5 hours. The product exhibited a monomodal pore distribution.

BET: 520 m$^2$/g
Pore diameter: 0.62 nm 1.6 Titanium dioxide-silicon dioxide glass 0.14 ml of tetraethoxytitanium, 10 ml of tetraethoxysilane and 8 ml of ethanol were dissolved successivefully in one another and 1.8 ml of 8 N hydrochloric acid were added with stirring. After gel formation had taken place, the t5 material was heated to 65° C. at a heating rate of 0.5° C./min, kept at 65° C. for 3 hours, heated at a heating rate of 0.2° C./min to 250° C. and calcined at this temperature for a further 3 hours. The product exhibited a monomodal pore distribution.

BET: 480 m$^2$/g
Pore diameter: 0.67 nm 1.7 Hydrophobized titanium dioxide-silicon dioxide-methylsilicon sesquioxide glass 0.133 ml of tetraisopropoxytitanium, 8 ml of tetraethoxysilanc, 1.8 ml of methyltriethoxysilane and 7.9 ml of ethanol were dissolved successively in one another and 1.98 ml of 8 N hydrochloric acid were added with stirring. After gel formation and hardening of the gel had taken place, this was heated under a protective gas to 65° C. at a heating rate of 0.2° C./min, kept at 65° C. for 3 hours, heated at a heating rate of 0.2° C./min to 250° C. and calcined at this temperature for a further 3 hours. The product exhibited a monomodal pore distribution.

BET: 540 m$^2$/g
Pore diameter: 0.70 nm 1.8 Hydrophobized iron-containing silicon dioxide-methylsilicon sesquioxide glass 8 ml of tetraethoxysilane, 1.8 ml of methyltriethoxysilane, 0.5 g of iron acetylacetonate and 8 ml of ethanol were dissolved successively in one another and 2 ml of 8 N hydrochloric acid were added with stirring. After gel formation and hardening of the gel had taken place, this was heated under protective gas to 65° C. at a heating rate of 0.2° C./min, kept at 65° C. for 3 hours, heated at a heating rate of 0.2° C./min to 230° C. and calcined at this temperature for a further 5 hours. The product exhibited a monomodal pore distribution.

BET: 420 m$^2$/g
Pore diameter: 0.61 nm

2. Reaction of the catalysts with benzene and dinitrogen monoxide/accompanying gas 2.1 Experimental conditions 2 cm$^3$ of catalyst were packed into a tubular reactor having an internal diameter of 8 mm. The catalyst was ground, in advance, to a particle size of 500–1000 µm. The reaction compartment was heated to the preset temperature. The temperature was monitored via a thermocouple. The amounts of benzene and gas were continuously added in gas form, the gas flow rate was set to 60 cm$^3$/min. The pressure was about 760 mmHg. The molar ratio of benzene to oxidizing agent in the gas compartment was 1:5 in this case. For laboratory experiments, the carrier gas used was nitrogen. The gas composition was analyzed by a GC/MS system. The zeolites used were Fe-ZSM-5 from the UOP company and ZSM-5 (iron-free) from the VAW company.

2.2 Results

| | Experiment Number | Catalyst | Temperature (° C.) | Composition of oxidizing agent (% by volume) | Benzene conversion rate (%) | Selectivity (%) |
|---|---|---|---|---|---|---|
| not according to the invention | 1. | iron-containing zeolite ZSM-5 | 375 | 100 N$_2$O | 7 | 97 |
| not according to the invention | 2. | iron-containing zeolite ZSM-5 | 425 | 100 N$_2$O | 13 | 85 |
| not according to the invention | 3. | zeolite ZSM-5 | 375 | 99 N$_2$O/1 H$_2$O | 0 | 0 |
| according to the invention | 4. | porous glass of Example 1.1 | 375 | 99 N$_2$O/1 H$_2$O | 0.5 | 50 |
| according to the invention | 5. | 100% ZSM-5/ 100% porous glass of Example 1.1 | 375 | 99 N$_2$O/1 H$_2$O | 2 | 59 |
| according to the invention | 6. | porous glass of Example 1.1 | 375 | 100 N$_2$O | 2 | 55 |
| according to the invention | 7. | porous glass of Example 1.2 | 375 | 100 N$_2$O | 2 | 67 |
| according to the invention | 8. | porous glass of Example 1.3 | 375 | 100 N$_2$O | 1 | 55 |
| according to the invention | 9. | porous glass of Example 1.4 | 375 | 100 N$_2$O | 2 | 49 |
| according to the invention | 10. | porous glass of Example 1.5 | 375 | 100 N$_2$O | 11 | 89 |
| according to the invention | 11. | porous glass of Example 1.6 | 375 | 100 N$_2$O | 1 | 51 |
| according to the invention | 12. | porous glass of Example 1.7 | 375 | 100 N$_2$O | 6 | 91 |
| according to the invention | 13. | porous glass of Example 1.8 | 375 | 100 N$_2$O | 13 | 95 |
| according to the invention | 14. | porous glass of Example 1.8 | 350 | 100 N$_2$O | 12 | 99 |
| according to the invention | 15. | porous glass of Example 1.8 | 375 | 90 N$_2$O/10 H$_2$O | 10 | 96 |
| according to the invention | 16. | iron-containing zeolite ZSM-5 | 375 | 90 N$_2$O/10 H$_2$O | 0 | 0 |
| according to the invention | 17. | porous glass of Example 1.8 | 375 | 99 N$_2$O/1 NH$_3$ | 3 | 85 |
| according to the invention | 18. | porous glass of Example 1.8 | 375 | 95 N$_2$O/5 air | 4 | 92 |
| according to the invention | 19. | porous glass of Example 1.8 | 375 | 99 N$_2$O/1 O$_2$ | 5 | 79 |

Obviously, numerous modifications and variations of the present invention are possible in light of the above teachings. It is, therefore, to be understood that within the scope of the appended claims, the invention may be practiced otherwise than as specifically described herein.

What is claimed is:

1. A process for the preparation of a hydroxyl-containing aromatic compound by catalytic oxidation, comprising carrying out the catalytic oxidation of the aromatic compound by a dinitrogen-monoxide-containing gas in the presence of a porous glass at a temperature of from about 100 to about 800° C.

2. The process as claimed in claim 1, wherein the aromatic compound is benzene.

3. The process as claimed in claim 1, wherein the dinitrogen-monoxide-containing gas comprises from 5 to 100% by volume dinitrogen monoxide and from 0 to 95% by volume of another gas.

4. The process as claimed in claim 1, wherein the dinitrogen-monoxide-containing gas comprises from 80 to 100% by volume dinitrogen monoxide and from 0 to 20% by volume of another gas.

5. The process as claimed in claim 3, wherein the other gas is selected from the group consisting of air, oxygen, nitrogen, noble gases, carbon dioxide, steam, ammonia and mixtures thereof.

6. The process as claimed in claim 1, wherein the mean pore size of the porous glass is between 0.1 and 1.0 nm.

7. The process as claimed in claim 1, wherein the catalytic oxidation is carried out at a temperature of from about 200 to about 700° C.

8. The process as claimed in claim 7, wherein the catalytic oxidation is carried out at a temperature of from about 250 to about 550° C.

9. The process as claimed in claim 1, wherein the total surface area of the porous glass in the dry state is at least about 50 $m^2/g$.

10. The process as claimed in claim 9, wherein the total surface area of the porous glass in the dry state is between about 50 and about 5000 $m^2/g$.

11. The process as claimed in claim 9, wherein the total surface area of the porous glass in the dry state is between about 75 and about 1500 $m^2/g$.

12. The process as claimed in claim 1, wherein the porous glass is prepared by the sol-gel process and consists of at least about 50% by weight of at least one oxide of an element of main group 3, of main group 4, of subgroup 3 or of subgroup 4 of the Periodic Table of the Elements, including the lanthanides and actinides.

* * * * *